(12) United States Patent
Lin

(10) Patent No.: US 11,357,907 B2
(45) Date of Patent: Jun. 14, 2022

(54) APPARATUS, SYSTEM, AND METHOD OF GAS INFUSION TO ALLOW FOR PRESSURE CONTROL OF IRRIGATION IN A SURGICAL SYSTEM

(71) Applicant: Johnson & Johnson Surgical Vision, Inc., Irvine, CA (US)

(72) Inventor: Justin Lin, Tustin, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 368 days.

(21) Appl. No.: 15/429,598

(22) Filed: Feb. 10, 2017

(65) Prior Publication Data

US 2018/0228962 A1 Aug. 16, 2018

(51) Int. Cl.
*A61M 3/02* (2006.01)
*A61F 9/007* (2006.01)

(52) U.S. Cl.
CPC ....... *A61M 3/0254* (2013.01); *A61F 9/00736* (2013.01); *A61F 9/00745* (2013.01); *A61M 3/022* (2014.02); *A61M 3/0208* (2014.02); *A61M 3/0237* (2013.01); *A61M 3/0241* (2013.01); *A61M 2205/502* (2013.01); *A61M 2210/0612* (2013.01)

(58) Field of Classification Search
CPC combination set(s) only.
See application file for complete search history.

(56) References Cited

U.S. PATENT DOCUMENTS

| | | | |
|---|---|---|---|
| 1,455,235 | A | 5/1923 | Townsend et al. |
| 2,208,550 | A | 7/1940 | Shapiro |
| 2,373,124 | A | 4/1945 | Frank |
| 2,413,710 | A | 1/1947 | Jason |
| 2,542,461 | A | 2/1951 | Bay |
| 2,716,517 | A | 8/1955 | Tollberg |
| 2,844,351 | A | 7/1958 | Charles et al. |
| 2,954,806 | A | 10/1960 | Kerr |
| 3,693,613 | A | 9/1972 | Kelman |
| 3,812,855 | A | 5/1974 | Banko |
| 3,838,691 | A | 10/1974 | Paludan et al. |

(Continued)

FOREIGN PATENT DOCUMENTS

| | | |
|---|---|---|
| EP | 1356834 A2 | 10/2003 |
| EP | 1428541 A2 | 6/2004 |

(Continued)

OTHER PUBLICATIONS

Alcon, Centurion Vision System: Insights and Experiences on Leveraging Innovative Phaco Technology, 2015, 8 pages.

(Continued)

*Primary Examiner* — Brandy S Lee
(74) *Attorney, Agent, or Firm* — Johnson & Johnson Surgical Vision, Inc.

(57) ABSTRACT

The disclosed apparatus, system and method may include at least a surgical fluid container that includes a fluid reservoir capable of containing the surgical fluid and a gas pressure pocket applied to the surgical fluid therewithin; a first external port extending from outside the fluid reservoir into fluid communication with the surgical fluid within the fluid reservoir; and a second external port extending directly from outside the fluid reservoir into the gas pressure pocket.

20 Claims, 3 Drawing Sheets

(56) References Cited

U.S. PATENT DOCUMENTS

| | | | |
|---|---|---|---|
| 3,931,818 A | 1/1976 | Goldowsky | |
| 3,973,602 A | 8/1976 | Kruse | |
| 4,052,987 A | 10/1977 | Wuchinich et al. | |
| 4,156,187 A | 5/1979 | Brumbach et al. | |
| 4,180,074 A | 12/1979 | Murry et al. | |
| 4,186,848 A | 2/1980 | Walter | |
| 4,221,308 A | 9/1980 | Goodall | |
| 4,292,969 A | 10/1981 | Raible et al. | |
| 4,328,803 A | 5/1982 | Pape | |
| 4,343,824 A | 8/1982 | Caldwell | |
| 4,361,148 A | 11/1982 | Shackleford et al. | |
| 4,425,123 A | 1/1984 | Di Salvo | |
| 4,548,205 A | 10/1985 | Armeniades et al. | |
| 4,570,898 A | 2/1986 | Staeubli | |
| 4,620,564 A | 11/1986 | Ekholmer | |
| 4,813,927 A | 3/1989 | Morris et al. | |
| 4,832,685 A | 5/1989 | Haines | |
| 4,841,984 A | 6/1989 | Armeniades et al. | |
| 4,900,301 A | 2/1990 | Morris et al. | |
| 4,921,477 A | 5/1990 | Davis | |
| 4,926,856 A | 5/1990 | Cambio, Jr. et al. | |
| 5,032,111 A | 7/1991 | Morris et al. | |
| 5,047,009 A | 9/1991 | Morris et al. | |
| 5,112,019 A | 5/1992 | Metzler et al. | |
| 5,176,629 A | 1/1993 | Kullas et al. | |
| 5,234,038 A | 8/1993 | Mitchell et al. | |
| 5,242,404 A | 9/1993 | Conley et al. | |
| 5,246,422 A | 9/1993 | Favre | |
| 5,341,836 A | 8/1994 | Doherty | |
| 5,342,293 A | 8/1994 | Zanger | |
| 5,360,398 A | 11/1994 | Grieshaber et al. | |
| 5,403,276 A | 4/1995 | Schechter et al. | |
| 5,417,246 A | 5/1995 | Perkins et al. | |
| 5,429,601 A | 7/1995 | Conley et al. | |
| 5,563,584 A | 10/1996 | Rader et al. | |
| 5,593,385 A | 1/1997 | Harrison et al. | |
| 5,593,392 A | 1/1997 | Starchevich | |
| 5,624,394 A | 4/1997 | Barnitz et al. | |
| 5,649,905 A | 7/1997 | Zanger et al. | |
| 5,676,650 A | 10/1997 | Grieshaber et al. | |
| 5,697,898 A | 12/1997 | Devine | |
| 5,700,240 A | 12/1997 | Barwick, Jr. et al. | |
| 5,733,256 A | 3/1998 | Costin | |
| 5,766,146 A | 6/1998 | Barwick, Jr. | |
| 5,795,328 A | 8/1998 | Barnitz et al. | |
| 5,810,765 A | 9/1998 | Oda | |
| 5,830,176 A | 11/1998 | Mackool | |
| 5,865,764 A | 2/1999 | Moorhead | |
| 5,910,110 A | 6/1999 | Bastable | |
| 5,954,971 A | 9/1999 | Pages et al. | |
| 6,013,049 A | 1/2000 | Rockley et al. | |
| 6,024,720 A | 2/2000 | Chandler et al. | |
| 6,083,193 A | 7/2000 | Kadziauskas et al. | |
| 6,149,621 A | 11/2000 | Makihara | |
| 6,159,175 A | 12/2000 | Strukel et al. | |
| 6,179,808 B1 | 1/2001 | Boukhny et al. | |
| 6,241,700 B1 | 6/2001 | Leukanech | |
| 6,261,283 B1 | 7/2001 | Morgan et al. | |
| 6,261,297 B1 | 7/2001 | Kadziauskas et al. | |
| 6,280,408 B1* | 8/2001 | Sipin | A61M 5/1483 604/65 |
| 6,283,937 B1 | 9/2001 | Takamatsu et al. | |
| 6,290,690 B1 | 9/2001 | Huculak et al. | |
| 6,391,000 B1* | 5/2002 | Belikan | A61M 3/0233 604/65 |
| 6,491,661 B1 | 12/2002 | Boukhny et al. | |
| 6,511,454 B1 | 1/2003 | Nakao et al. | |
| 6,527,745 B1 | 3/2003 | Kanda et al. | |
| 6,730,106 B2 | 5/2004 | Kanda et al. | |
| 6,780,166 B2 | 8/2004 | Kanda et al. | |
| 6,849,059 B2 | 2/2005 | Suzuki et al. | |
| 6,875,194 B2 | 4/2005 | Mackool | |
| 6,899,694 B2 | 5/2005 | Kadziauskas et al. | |
| 6,908,451 B2 | 6/2005 | Brody et al. | |
| 6,969,032 B2 | 11/2005 | Olivera et al. | |
| 6,997,896 B2 | 2/2006 | Novak | |
| 7,001,356 B2 | 2/2006 | Kadziauskas et al. | |
| 7,018,355 B2 | 3/2006 | Kadziauskas et al. | |
| 7,197,567 B1 | 3/2007 | Fitzgerald | |
| 7,563,242 B2 | 7/2009 | Yaguchi et al. | |
| 7,867,191 B2 | 1/2011 | Suzuki | |
| 7,967,777 B2 | 6/2011 | Edwards et al. | |
| 8,070,712 B2 | 12/2011 | Muri et al. | |
| 8,287,486 B2 | 10/2012 | Injev | |
| 8,388,582 B2 | 3/2013 | Eubanks et al. | |
| 8,679,089 B2 | 3/2014 | Berlin | |
| 9,205,186 B2 | 12/2015 | Tarkeshian et al. | |
| 9,433,723 B2 | 9/2016 | Steen et al. | |
| 9,445,943 B2 | 9/2016 | Wilson et al. | |
| 9,511,184 B2 | 12/2016 | Woolford et al. | |
| 10,729,581 B2 | 8/2020 | Boukhny et al. | |
| 2001/0004684 A1 | 6/2001 | Morgan et al. | |
| 2001/0023331 A1 | 9/2001 | Kanda et al. | |
| 2002/0019601 A1 | 2/2002 | Wada | |
| 2002/0019607 A1 | 2/2002 | Bui | |
| 2002/0085952 A1 | 7/2002 | Ellingboe et al. | |
| 2003/0163138 A1 | 8/2003 | Nazarifar et al. | |
| 2003/0201412 A1 | 10/2003 | Brody et al. | |
| 2004/0108340 A1 | 6/2004 | Witt | |
| 2004/0116846 A1 | 6/2004 | Olivera et al. | |
| 2005/0237503 A1 | 10/2005 | Kubo | |
| 2006/0100580 A1 | 5/2006 | Muller | |
| 2006/0149301 A1 | 7/2006 | Claus | |
| 2008/0033349 A1 | 2/2008 | Suzuki | |
| 2008/0114290 A1 | 5/2008 | King et al. | |
| 2010/0145302 A1 | 6/2010 | Cull et al. | |
| 2010/0280434 A1 | 11/2010 | Raney et al. | |
| 2010/0280435 A1 | 11/2010 | Raney et al. | |
| 2010/0292631 A1 | 11/2010 | Holden et al. | |
| 2011/0054385 A1 | 3/2011 | Eichler | |
| 2011/0112472 A1 | 5/2011 | Jacobson et al. | |
| 2011/0282273 A1 | 11/2011 | Evans et al. | |
| 2011/0295191 A1 | 12/2011 | Injev | |
| 2011/0313343 A1 | 12/2011 | Milutinovic et al. | |
| 2012/0215160 A1 | 8/2012 | Valenti et al. | |
| 2012/0232466 A1 | 9/2012 | Kuebler et al. | |
| 2013/0131578 A1 | 5/2013 | Stalmans et al. | |
| 2013/0138035 A1 | 5/2013 | Huculak et al. | |
| 2013/0237900 A1 | 9/2013 | Hauger | |
| 2013/0245543 A1 | 9/2013 | Gerg et al. | |
| 2013/0267779 A1 | 10/2013 | Woolford et al. | |
| 2014/0074013 A1 | 3/2014 | Mcgary et al. | |
| 2014/0114237 A1 | 4/2014 | Gordon et al. | |
| 2014/0276639 A1* | 9/2014 | Tarkeshian | A61M 3/0216 604/521 |
| 2016/0095750 A1 | 4/2016 | Raney et al. | |
| 2016/0100981 A1 | 4/2016 | Klomp | |
| 2016/0220751 A1 | 8/2016 | Mallough et al. | |
| 2017/0151090 A1 | 6/2017 | Raney et al. | |
| 2017/0151092 A1 | 6/2017 | Raney et al. | |
| 2017/0151376 A1 | 6/2017 | Raney et al. | |
| 2017/0151377 A1 | 6/2017 | Raney et al. | |
| 2017/0151378 A1 | 6/2017 | Raney et al. | |
| 2017/0151379 A1 | 6/2017 | Raney et al. | |
| 2017/0273826 A1* | 9/2017 | Sanchez, Jr. | A61F 9/0017 |
| 2019/0321222 A1 | 10/2019 | Lieu | |

FOREIGN PATENT DOCUMENTS

| | | |
|---|---|---|
| WO | 9112034 A1 | 8/1991 |
| WO | 9418894 A1 | 9/1994 |
| WO | 0217833 A1 | 3/2002 |
| WO | 2009112251 A1 | 9/2009 |
| WO | 2012092018 A1 | 7/2012 |

OTHER PUBLICATIONS

Johansson B, "Adaptive Fluidics: A Complete Game Changer, Automated Aspiration control, Dynamic Infusion Compensation, and a Controlled Surgical Environment," Jun. 2019, pp. 1-2.

Yeu E., "A Clinical Study Review—the Role of Active Fluidics and Torsional Phaco Power in Providing a Stable and Efficient Cataract Surgery Environment," US Ophthalmic Review, Mar. 2018, retrieved

(56) References Cited

OTHER PUBLICATIONS from Internet URL: [https://www.touchophthalmology.com/ebooks/ophthalmology/USOPHTH111/index.html?page=34], 12 pages.

* cited by examiner

APPARATUS, SYSTEM, AND METHOD OF GAS INFUSION TO ALLOW FOR PRESSURE CONTROL OF IRRIGATION IN A SURGICAL SYSTEM

BACKGROUND

Field of the Disclosure

The present disclosure relates to medical devices and systems, and, more specifically, to an apparatus, system, and method of gas infusion to allow for pressure control of irrigation in a surgical system, such as in a phacoemulsification system.

Description of the Background

Phacoemulsification is a medically recognized technique utilized for crystalline lens removal, and is one type of ophthalmic surgery. Phacoemulsification includes making a corneal and/or scleral incision, and the insertion of a phacoemulsification handpiece, which is typically comprised of a needle that is ultrasonically driven, in order to emulsify, i.e., to liquefy or break up, the natural crystalline lens and/or an unhealthy aspect, such as a cataract, associated with the patient's eye.

The phacoemulsification handpiece is generally coupled to an irrigation source and an aspiration pump. The handpiece includes a distal tip for insertion within the anterior chamber of the patient's eye that emits ultrasonic energy to emulsify the crystalline lens or the unhealthy aspect. The handpiece further includes a sleeve that surrounds at least a portion of the needle that comprises at least one irrigation port near the distal end of the sleeve, which is coupled to an irrigation source via an irrigation line, and an aspiration port at the distal tip of the needle, which is coupled to an aspiration pump via an aspiration line. Fluid from the irrigation source, which is typically an elevated bottle or bag of saline solution, is irrigated into the eye via the irrigation line and the irrigation port, and the irrigation fluid and emulsified material are aspirated from the eye by the aspiration pump via the aspiration port and the aspiration line.

Other ophthalmic surgical techniques also typically include irrigation and aspiration of the eye. Such other ophthalmic procedures may or may not include the destruction, alteration or removal of features of the natural eye and/or unhealthy aspects of the eye.

As such, ophthalmic surgical systems typically provide a control console to control the aforementioned one or more fluid pressure operated surgical instruments. The control console provides the pressure signals for operating the instruments, and may include several different types of human actuatable controllers for controlling these signals. One such actuatable controller is often a footpedal assembly, which the surgeon can use to control the referenced surgical instrumentation.

Conventional footpedal assemblies may use a variety of pneumatic and electrical actuators to provide the control signals. In pneumatic footpedal assemblies, pneumatic fluid enters the footpedal assembly through an inlet port, which is connected to a pneumatic supply. The amount of pneumatic fluid leaving the footpedal assembly is proportional to the amount of depression on the footpedal of the assembly. Footpedal assemblies which employ electrical actuators may use a potentiometer attached to the pedal. In this case, as the pedal is pressed by the operator, the resistance of the potentiometer changes.

The irrigation fluid flow controlled during ophthalmic surgeries is the result of the pressure to which the irrigation fluid is subjected. Typically, irrigation pressure is controlled in a sterilized environment through one of three methods—namely gravity, non-contact pumping, or increased head pressure. In order to control irrigation pressure, the industry standard for decades has been the aforementioned use of a gravity-based system in the form of an intravenous bag pole having thereon a balanced salt solution (BSS) bottle or bag. In short, the raising of the bottle or bag raises the irrigation pressure on the irrigation fluid based on the enhanced pull of gravity.

As mentioned above, alternate known methodologies may control the pressure by manipulating head pressure at the liquid head within the bottle or bag. Head pressure is typically manipulated by a common technique known as vented gas forced infusion, in which a metal tube is inserted through the bottom of the bottle or bag, is passed through the fluid within the bottle or bag, and the air pocket in the bottle or bag atop the liquid is then pressurized by providing gas through the metal tube to create an increase in head pressure. The head pressure of the fluid may also be depressurized through the drawing of gas through the metal tube.

However, the insertion of a metal tube in order to control head pressure also offers significant disadvantages. For example, the metal tube is expensive to integrate into a consumable pack, and the small orifice and delivery volume does not allow for quick pressurization or depressurization.

Therefore, the need exists to provide an apparatus, system, and method of gas infusion to allow for pressure control of irrigation in a surgical system.

SUMMARY

The disclosed apparatus, system and method may include at least a surgical fluid container that includes a fluid reservoir capable of containing the surgical fluid and a gas pressure pocket applied to the surgical fluid therewithin; a first external port extending from outside the fluid reservoir into fluid communication with the surgical fluid within the fluid reservoir; and a second external port extending directly from outside the fluid reservoir into the gas pressure pocket.

Also included may be an irrigation system that includes a phacoemulsification console and an irrigation bottle or bag. The irrigation bottle or bag may include a fluid reservoir; and at least two ports in fluid communication with the fluid reservoir, wherein a first of the at least two ports is in fluid communication with irrigation fluid in the fluid reservoir, and wherein a second of the at least two ports is in fluid communication with a gas pressure pocket that is in fluid communication with the irrigation fluid. The varied pressure may be provided to the gas pressure pocket pursuant to controls by the phacoemulsification console, such that a flow of the irrigation fluid varies responsive to the varied pressure.

A method for providing surgical fluid may include receiving an instruction to increase head pressure on the surgical fluid; providing a gas to a surgical fluid reservoir containing the surgical fluid via a dedicated air port and responsive to the receiving of the instruction; and outputting the surgical fluid at a flow rate responsive to a varied pressure resulting from the providing of the gas.

Thus, the disclosed embodiments provide at least an apparatus, system, and method of gas infusion to allow for pressure control of irrigation in a surgical system.

BRIEF DESCRIPTION OF THE FIGURES

Referring now to the figures incorporated herein, shown are non-limiting embodiments of the present disclosure, wherein like numerals represent like elements, and wherein.

DETAILED DESCRIPTION

Figure 1:
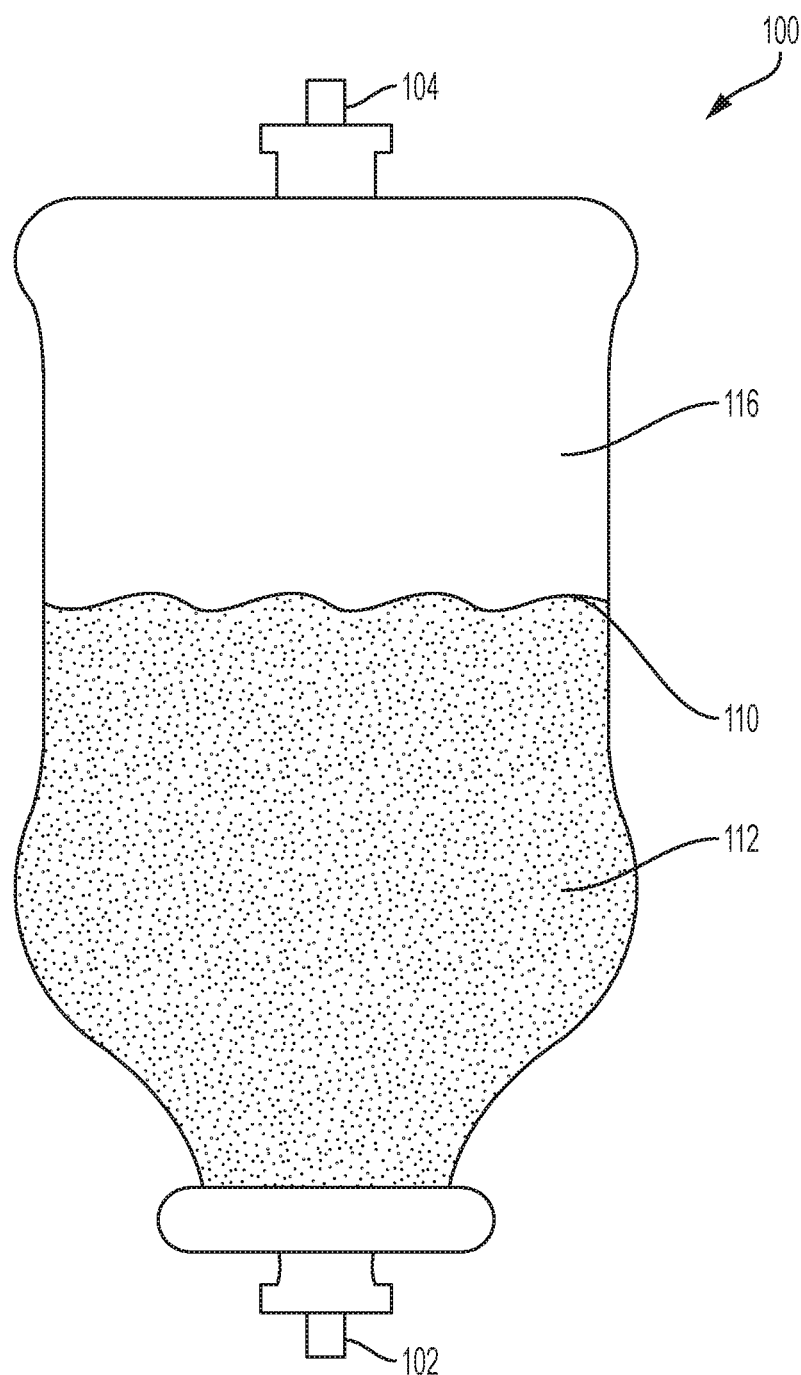
FIG. 1 is a diagram illustrating an exemplary irrigation bag or bottle according to certain of the embodiments.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

The terminology used herein is for the purpose of describing particular exemplary embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "engaged to", "connected to" or "coupled to" another element or layer, it may be directly on, engaged, connected or coupled to the other element or layer, or intervening elements or layers may be present, unless clearly indicated otherwise. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

Certain types of ocular dysfunction, such as cataracts, are commonly treated with surgical procedures, such as to remove the natural lens from the eye and replace it with a clear artificial lens. More particularly and by way of example, phacoemulsification refers to a surgery, often employed when a patient suffers from cataracts, in which the eye's natural lens is emulsified by applying ultrasonic energy to the lens with a handpiece. Once the lens is emulsified, it is aspirated from the eye by applying a vacuum tube to the emulsified lens material. During the procedure, irrigation is performed, and aspirated material replaced, using a balanced salt solution, thereby maintaining necessary pressure in the interior of the eye. The emulsified and aspirated lens is then typically replaced with a clear artificial intraocular lens (IOL).

To perform the afore-discussed and similar procedures, a surgeon often utilizes a computer-controlled system of specialized equipment called a phacoemulsification system to control and execute the ultrasonic emulsification, irrigation, and aspiration of the natural lens of the eye prior to inserting the IOL. Phacoemulsification systems use various computer programs for performing these various tasks, which are controlled in part by adjusting settings of these programs to drive motors and pumps, for example, which emulsify, irrigate, and aspirate the subject lens material and which do other tasks necessary to complete the surgery. These control programs may receive control signals from the system console, and/or from peripheral elements linked to the system console. Such peripheral control elements may include, by way of example, one or more footpedals.

During the procedure, information such as the amount of vacuum applied to aspirate, the flow rate, a microscopic view of the operating field, the irrigation pressure, and the like, may be displayed on and at least partially controllable from a user interface of the phacoemulsification system console, or on a separate screen, computer, or other viewing device. At least some of this data and functionality is controlled to inform and improve current and subsequent procedures.

The embodiments provide at least a dual ported surgical fluid reservoir capable of providing irrigation. The reservoir is suitable to readily receive gas, responsive to one or more control signals, to pressurize and depressurize head pressure within the reservoir. The improved and refined control of the head pressure thus provided allows for a refined control of irrigation in a surgical system, such as a phacoemulsification system.

More particularly and as illustrated in FIG. 1, a reservoir 100, such as a BSS source reservoir 100, may be provided with two ports 102, 104. One of the ports 102 may be for irrigation, and the other 104 for air or other gas input or withdrawal.

The port 104 may allow for the providing of pressure, or depressurization, at the head 110 of the irrigation fluid 112 in the surgical system. This pressure to the head 110 may be provided through the port 104 into the air pocket 116 provided above the irrigation fluid 112 (which may be the aforementioned BSS in certain of the embodiments). The use of the port 104 in the disclosed embodiments may allow for the avoidance of the use of a metal tube to provide increased head pressure, as is done in the known art. The skilled artisan will appreciate that the placement of the port 104 in FIG. 1 is exemplary in nature only, and that port 104 may reside at any point along the reservoir 100 at which access is available to air pocket 116, including via one or more tubes that may pass through portions of air pocket 116 and/or through fluid 112 (not shown).

Accordingly, and unlike other known methodologies of advancing head pressure in a surgical fluid system such as the aforementioned insertion of a metal tube to advance head pressure, the disclosed embodiments provide an enlarged orifice that enables quick volume pressurization and depressurization at the head of the irrigation (or other surgical) fluid. More particularly, the availability of higher air flow rates into and out of the reservoir in the disclosed embodiments allows for expedited and improved control, such as by providing both fine and coarse adjustment, of fluid pressure in a surgical system, such as irrigation pressure in a phacoemulsification system.

Figure 2:
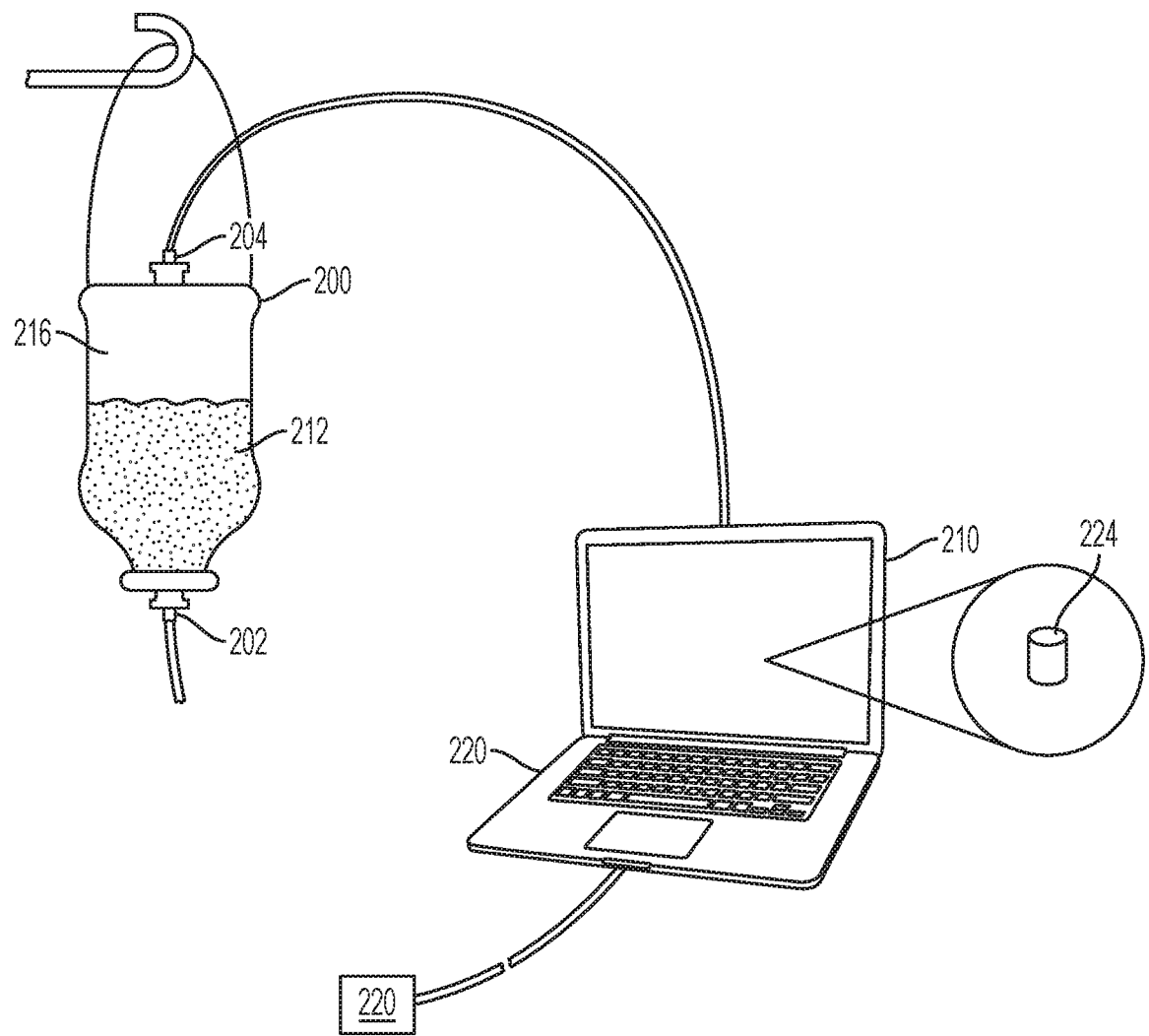
FIG. 2 is a diagram illustrating an exemplary irrigation system according to certain of the embodiments.

FIG. 2 illustrates a dual port 202, 204 irrigation system for control by a surgical console 210, such as a phacoemulsification console 210. As illustrated, an irrigation source 200, such as a balanced salt solution bag or bottle, is provided as a reservoir/fluid source. The source 200 is illustrated as having two ports 202, 204, such as one port atop the reservoir and another at the bottom of the reservoir.

In the illustration, the upper port 204 may be positioned such that it leads to the air pocket 216 of the irrigation reservoir 200 without being impeded by the liquid 212 in the reservoir. Thereby, the illustrated upper port 204 allows air to flow directly from the air pressure system of phacoemulsification console 210 into the air pocket 216 of the reservoir 200. This air flow accordingly increases or decreases the air pressure placed on the irrigation liquid 212 correspondent to the volume of air pushed into the bottle or bag 200 or withdrawn from the bottle or bag 200 by the console 210 at the air pocket 216.

The phacoemulsification console 210 connective to the irrigation source 200 may be instructed, either by an operator, such as by actuation of a button, handle, or footpedal 220, or automatically such as upon reaching a trigger 224 pre-programmed into console 210, to pump gas into or vent gas from the air pocket 216 via the port 204. This actuation of the port 204 may thus allow the user and/or the console 210 to increase or decrease the pressure on the irrigation liquid 212 very quickly, and with both fine and coarse control. This enables an expedited response to any surgical conditions, such as abnormal surgical conditions, i.e., post-occlusion surge, due at least to the improved efficiency in the input orifice 204 over the known art.

An expedited and refined responsiveness in the head pressure of the irrigation liquid allows for a closed-loop dynamic irrigation system, as illustrated in FIG. 2. That is, the response of head pressure to surgical conditions may be automated based on surgical factors monitored by the console 210, such as based on indications from sensors at, near, or otherwise viewing or measuring parameters of the eye. Needless to say, surgical outcomes are consequently improved through the use of the embodiments.

Figure 3:
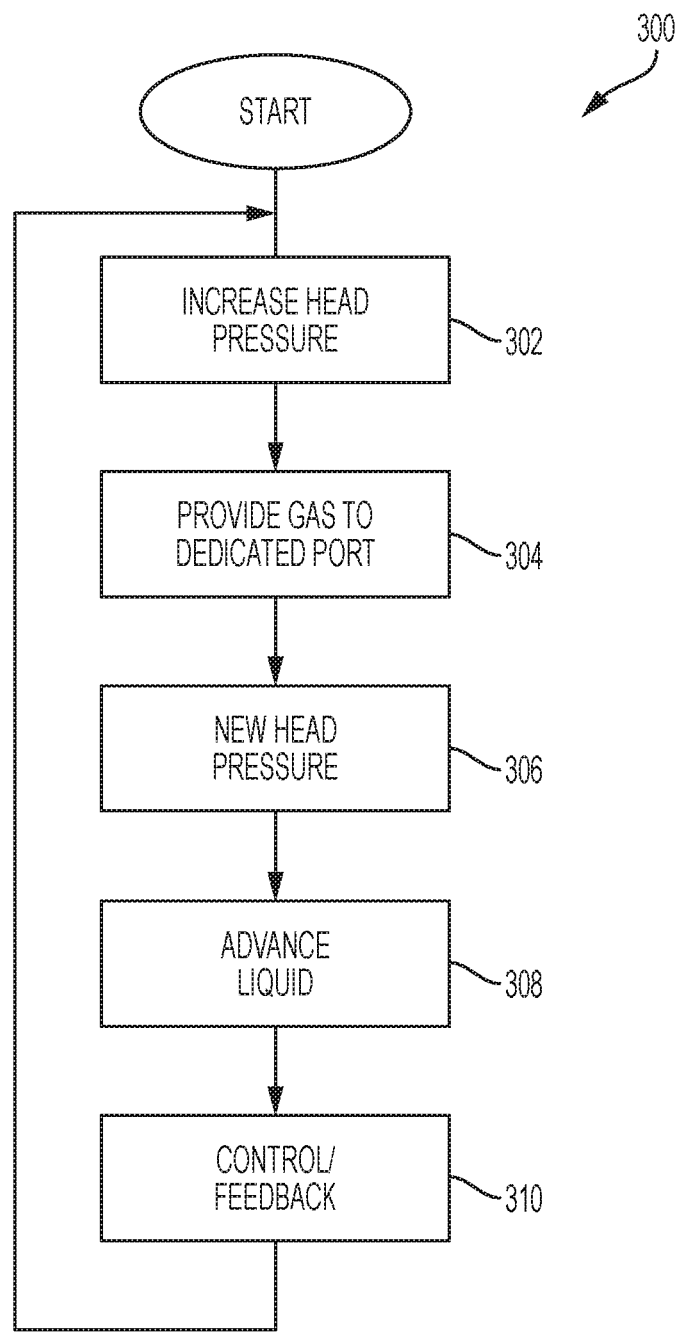
FIG. 3 is a flow diagram illustrating an exemplary method according to certain of the embodiments.

FIG. 3 is a flow diagram illustrating a method 300 in accordance with the embodiments. In the illustration, at step 302 an instruction to increase head pressure in a surgical fluid system is received. The surgical system may be, for example, an irrigation system in a phacoemulsification system.

At step 304, air or another gas is provided by the receiver of the instruction at step 302 to a surgical fluid reservoir via a dedicated port. At step 306, the head pressure on the fluid in the reservoir is increased commensurate with the air delivered at step 304. The fluid may be, for example, a balanced salt solution.

The fluid is advanced, commensurate with the increased pressure delivered at step 306, from a second port not in direct fluid communication with the port at step 308. At step 310, the output of the fluid according to step 308 may be controlled via control signaling, sensing, and/or feedback using any known methodologies, such as in-line buffers, port limiters, or the like.

Although the exemplary embodiments may be discussed herein with respect to a phacoemulsification system, those skilled in the art will appreciate that the disclosed apparatus, system, and method may be applied to any medical, pharmaceutical, or surgical system which requires expedited and refined adjustments in the head pressure on a surgical fluid. Moreover, the embodiments allow for the liquid and closed surgical system to remain sterile, at least in that no pump is needed for insertion between a liquid source and an application.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:
1. A surgical fluid container, comprising:
 a fluid reservoir capable of containing a surgical fluid and a gas pressure pocket applied to the surgical fluid therewithin, wherein the fluid reservoir comprises a top and a bottom and the gas pressure pocket is provided above the surgical fluid;

a first external port extending from outside the bottom of the fluid reservoir into fluid communication with the surgical fluid within the fluid reservoir; and a second external port extending directly from outside the top of the fluid reservoir into the gas pressure pocket, wherein the second external port comprises an orifice configured to enable quick pressurization and depressurization of the gas pressure pocket.

2. The container of claim 1, wherein the first external port comprises an irrigation port.

3. The container of claim 1, wherein the surgical fluid comprises a balanced salt solution.

4. The container of claim 1, wherein the first external port is fluidly coupled with a phacoemulsification handpiece.

5. The container of claim 1, wherein the second external port is capable of receiving gas pressure.

6. The container of claim 1, wherein the second external port is capable of outputting gas pressure.

7. An irrigation system, comprising:
a phacoemulsification console;
an irrigation source, comprising:
a fluid reservoir capable of containing an irrigation fluid and a gas pressure pocket applied to the irrigation fluid therewithin, wherein the fluid reservoir comprises a top and a bottom and the gas pressure pocket is provided above the irrigation fluid and is in fluid communication with the irrigation fluid; and
at least two ports in fluid communication with the irrigation source, wherein a first of the at least two ports is located at the bottom of the fluid reservoir and is in fluid communication with the irrigation fluid in the fluid reservoir, and wherein a second of the at least two ports is an orifice configured to enable quick volume pressurization and depressurization of the gas pressure pocket and is located at the top of the fluid reservoir and is in fluid communication with the gas pressure pocket;
wherein varied pressure is provided to the gas pressure pocket pursuant to controls by the phacoemulsification console, such that a flow of the irrigation fluid from the first of the at least two ports varies responsive to the varied pressure.

8. The system of claim 7, wherein the second of the at least two ports is in fluid communication with the gas pressure pocket via at least one tube that passes through the irrigation fluid.

9. The system of claim 7, wherein the varied pressure comprises direct air flow from the phacoemulsification console.

10. The system of claim 7, wherein the varied pressure comprises decreased pressure, thereby producing decreased irrigation fluid flow.

11. The system of claim 7, wherein the varied pressure comprises increased pressure, thereby producing increased irrigation fluid flow.

12. The system of claim 7, wherein the controls are responsive to a user input to the phacoemulsification console.

13. The system of claim 12, wherein the user input comprises input to a peripheral of the phacoemulsification console.

14. The system of claim 13, wherein the peripheral comprises a footpedal.

15. The system of claim 7, wherein the irrigation fluid comprises a balanced salt solution.

16. The system of claim 7, wherein the irrigation source is selected from the group consisting of a bag and bottle.

17. A method for adjusting the flow of a surgical fluid, comprising:
providing a fluid reservoir capable of containing a surgical fluid and a gas pressure pocket applied to the surgical fluid therewithin, wherein the fluid reservoir comprises a top and a bottom and the gas pressure pocket is provided above the surgical fluid;
receiving an instruction to increase head pressure on the surgical fluid;
providing a gas to the fluid reservoir containing the surgical fluid via a dedicated gas port and responsive to the receiving of the instruction, wherein the dedicated gas port is an orifice configured to enable quick volume pressurization and depressurization of the gas pressure pocket and extends directly from outside the top of the fluid reservoir into the gas pressure pocket; and
outputting the surgical fluid via an irrigation port at a flow rate responsive to a varied pressure resulting from the providing of the gas, wherein the irrigation port extends from outside the bottom of the fluid reservoir into fluid communication with the surgical fluid within the fluid reservoir.

18. The method of claim 17, wherein the surgical fluid comprises a balanced salt solution.

19. The method of claim 17, wherein the gas provided is air.

20. The method of claim 17, wherein the receiving the instruction comprises receiving the instruction from a surgical console.

* * * * *